(12) United States Patent
Ghelfi et al.

(10) Patent No.: US 7,638,457 B2
(45) Date of Patent: Dec. 29, 2009

(54) NIOBIUM-DOPED VANADIUM/PHOSPHORUS MIXED OXIDE CATALYST

(75) Inventors: Federico Ghelfi, Crevalcore (IT); Gianluca Mazzoni, Torre Boldone (IT); Carlo Fumagalli, Albano San Alessandro (IT); Fabrizio Cavani, Modena (IT); Francesca Pierelli, Fano (IT)

(73) Assignee: Lonza S.p.A., Scanzorosciate (IT)

( * ) Notice: Subject to any disclaimer, the term of this patent is extended or adjusted under 35 U.S.C. 154(b) by 382 days.

(21) Appl. No.: 10/571,316

(22) PCT Filed: Sep. 15, 2004

(86) PCT No.: PCT/EP2004/010336

§ 371 (c)(1), (2), (4) Date: Mar. 16, 2006

(87) PCT Pub. No.: WO2005/025742

PCT Pub. Date: Mar. 24, 2005

(65) Prior Publication Data

US 2006/0173197 A1      Aug. 3, 2006

(30) Foreign Application Priority Data

Sep. 15, 2003   (EP) .................. 03425597

(51) Int. Cl.
  *B01J 27/00*   (2006.01)
  *B01J 27/198*  (2006.01)
  *B01J 23/00*   (2006.01)
  *C07D 307/60*  (2006.01)

(52) U.S. Cl. ............ 502/209; 502/208; 502/353; 549/233

(58) Field of Classification Search ........... 502/208, 502/209, 353; 549/233
  See application file for complete search history.

(56) References Cited

U.S. PATENT DOCUMENTS

| | | | |
|---|---|---|---|
| 3,255,211 A * | 6/1966 | Kerr ................... 549/260 |
| 4,147,661 A | 4/1979 | Higgins et al. |
| 4,594,433 A | 6/1986 | Suciu et al. |
| 4,654,425 A | 3/1987 | Suciu et al. |
| 4,668,652 A | 5/1987 | Fumagalli et al. |
| 4,732,885 A * | 3/1988 | Edwards et al. ......... 502/209 |
| 4,950,769 A * | 8/1990 | McCandless et al. ..... 549/257 |
| 5,019,545 A * | 5/1991 | Haddad et al. .......... 502/209 |
| 5,095,125 A * | 3/1992 | Haddad et al. .......... 549/259 |
| 5,137,860 A | 8/1992 | Ebner et al. |
| 5,474,960 A * | 12/1995 | Bremer et al. .......... 502/34 |
| 5,506,187 A * | 4/1996 | Haddad et al. .......... 502/209 |
| 5,847,163 A | 12/1998 | Mazzoni et al. |
| 6,734,135 B1 | 5/2004 | Albonetti et al. |
| 2004/0162217 A1 | 8/2004 | Albonetti et al. |

FOREIGN PATENT DOCUMENTS

| | | |
|---|---|---|
| EP | 0098039 | 1/1984 |
| EP | 0804963 | 11/1997 |
| EP | 1514598 A1 * | 3/2005 |
| WO | 00/72963 | 12/2000 |

OTHER PUBLICATIONS

Duarte De Farias, A.M., et al., Journal of Catalysis, Academic Press, Duluth, MN, US, vol. 208, No. 1 (May 15, 2002), pp. 238 to 246.
Hutchings, G.J., Appl. Catal., (1991), 72, 1-32.
Stud. Surf. Sci. Catal., "Preparation of Catalysts VI", vol. 91, Elsevier Science (1995) p. 1.
Mastuura, I.I., et al. Catal. Today, (1996), 28, 133-138.
Pries de Oliveira, P.G., et al., Catal. Today (2000), 57, 177-186.

* cited by examiner

*Primary Examiner*—Patricia L Hailey

(57) ABSTRACT

Disclosed is a process for the preparation of a modified vanadium/phosphorus mixed oxide catalyst for the partial oxidation of n-butane to maleic anhydride. The catalyst comprises vanadyl pyrophosphate as main component and niobium as a promoter element in an amount corresponding to an atomic ratio of vanadium to niobium in the range of 250:1 to 60:1. The catalyst exhibits improved activity, improved yield of maleic anhydride, and optimal performance from the very beginning of its catalytic lifetime.

36 Claims, No Drawings

NIOBIUM-DOPED VANADIUM/PHOSPHORUS MIXED OXIDE CATALYST

This application is a 371 national stage application of International (PCT) Application No. PCT/EP04/010336, filed on Sep. 15, 2004 that has priority benefit of European Patent Application No. 03425597.6, filed on Sep. 15, 2003.

The invention relates to a process for the production of a vanadium/phosphorus mixed oxide catalyst containing niobium (Nb) as promoter, to be used as the catalysts for the production of maleic anhydride by selective oxidation of n-butane, the catalyst obtainable by said process, and a process for the production of maleic anhydride utilizing said catalyst.

Maleic anhydride is a well known and versatile intermediate for the manufacture of unsaturated polyester resins, chemical intermediates as butanediol and tetrahydrofuran, pharmaceuticals and agrochemicals. It is produced by partial oxidation of aromatic (e.g., benzene) or non-aromatic (e.g., n-butane) hydrocarbons. The oxidation is performed in the gas phase, in the presence of a heterogeneous catalyst, in a fixed, fluidized, or riser bed reactor.

The main component of the catalyst for the oxidation of non-aromatic hydrocarbons like n-butane to maleic anhydride is vanadyl pyrophosphate, $(VO)_2P_2O_7$, which is obtained by thermal treatment of vanadyl acid orthophosphate hemihydrate of the formula $(VO)HPO_4.0.5H_2O$, acting as catalyst precursor.

Methods for preparing the precursor conventionally involve reducing a pentavalent vanadium compound under conditions which will provide vanadium in a tetravalent state (average oxidation number +4) and the reaction of the tetravalent vanadium with phosphoric acid.

Prior art describes many different procedures for this preparation, which in general involve the use of vanadium pentoxide ($V_2O_5$) as a source of vanadium (see e.g. U.S. Pat. No. 5,137,860 and EP 0 804 963 A1). Hydrogen chloride in aqueous solution is one of the reducing agents mentioned for the reduction of $V^{+5}$ to $V^{+4}$. Also used are organic reducing media like primary or secondary aliphatic alcohols or aromatic alcohols such as isobutyl alcohol and benzyl alcohol. The most used organic reducing agent is isobutyl alcohol since it combines optimal solvent and redox characteristics, thus favouring a complete redox reaction with formation of tetravalent vanadium, which is reacted with phosphoric acid to form the precursor vanadyl acid orthophosphate hemihydrate of the formula $(VO)HPO_4.0.5H_2O$.

Both vanadyl pyrophosphate and vanadyl acid orthophosphate hemihydrate may be modified by addition of a promoter element selected from the groups IA, IB, IIA, IIB, IIIA, IIIB, IVA, IVB, VA, VB, VIA, VIB and VIIIA of the periodic table of elements, or of mixtures of such elements.

Patent literature claims that the catalytic performance of vanadyl pyrophosphate can be substantially improved by addition of these elements. An exhaustive review of the promoters reported in the literature and of their role has been reported by G. J. Hutchings in *Appl. Catal.*, 1991, 72, 1-32, and in *Stud. Surf. Sci. Catal.* "Preparation of Catalysts VI", (G. Poncelet et al., Eds.), Vol. 91, Elsevier Science, Amsterdam, 1995, p. 1.

Prior art mentions niobium among the promoters that improve the catalytic performance of vanadyl pyrophosphate but the results obtained are not completely satisfactory.

1. I. Mastuura, et al. (*Catal. Today*, 1996, 28, 133-138) co-precipitate V and Nb in an aqueous solution and treat the precipitate with benzyl alcohol at reflux. The solid product obtained is activated in the presence of a reaction mixture comprising air and n-butane. The Nb modified catalysts show a higher activity, the best results are obtained for high promoter concentrations (atomic ratio V/Nb=4).

2. P. G. Pries de Oliveira, et al. (*Catal. Today*, 2000, 57, 177-186) prepare the VPO precursor in isobutyl alcohol and introduce $NbPO_4$ just before the nucleation of vanadyl acid orthophosphate hemihydrate. The catalyst precursor is activated in the reactor under butane/air atmosphere. The addition of Nb shortens the time required to reach stationary performances of the catalyst from 120 hours to 40 hours. A higher activity is reported for the promoted catalyst compared with the non-promoted catalyst. Best results are reported for high promoter concentrations (atomic ratio V/Nb=6.4).

3. A. M. Duarte de Farias et al. (*J. Catal.* 2002, 208, 238-246) solubilize Nb ethoxide into isobutyl alcohol and use it as a reducing agent to prepare the Nb modified catalyst precursor. The activation of the precursor is performed under reaction conditions. The Nb promoted catalyst (atomic ratio V/Nb=100) has a higher activity compared with the non-promoted VPO catalyst, however the authors state that the selectivity to maleic anhydride is not improved by Nb-doping.

4. R. Higgins, G. J. Hutchings (U.S. Pat. No. 4,147,661 (1979), assigned to ICI Ltd.) prepare the Nb promoted catalyst in isobutyl alcohol using hydrogen chloride gas as reducing agent. The patent uses high amounts of promoter (atomic ratio V/Nb=14) and performs the activation in the reaction tube in the presence of the reaction mixture air/n-butane.

To summarise, in the prior art, the positive effect of Nb is achieved using high amounts of promoter (low V/Nb atomic ratios: refs. 1, 2 and 4) and/or when the thermal treatment of the precursor, to transform it into vanadyl pyrophosphate, is done inside the reactor, with a mixture of n-butane/air (refs. 1, 2, 3 and 4). This implies a period of activation of the catalyst during which the conversion of n-butane and the yield of maleic anhydride are far from the optimal values and which is detrimental for commercial applications. Moreover, in the prior art the positive effect of Nb doping results in a more active catalyst, but, particularly when low amounts of Nb are used (ref. 3), the selectivity to maleic anhydride is not improved.

We have now found that a positive effect both on the activity of the catalyst and on its selectivity to maleic anhydride can be obtained by promoting the VPO catalyst with very low amounts of Nb. The positive effect is obtained by combining a specific method of preparation of the precursor with a specific thermal treatment of the precursor to transform it into the active catalyst vanadyl pyrophosphate. The P/V atomic ratio in the preparation mixture has an optimal value which is a function of the amount of Nb added. The preparation of the precursor is done in organic medium of suitable composition, avoiding the use of dangerous and corrosive reducing agents like HCl, which require special materials of construction. A further advantage of the present invention is that the thermal treatment of the precursor to transform it into the active catalyst vanadyl pyrophosphate is performed outside the reactor, so that the catalyst, when loaded into the reactor, gives optimal catalytic performances from the very beginning. According to the present invention the precursor can be advantageously prepared following the procedure described in the patent application WO 00/72963 (Lonza S.p.A.).

WO 00/72963 teaches a process for the preparation of a vanadium/phosphorus mixed oxide catalyst precursor in which the reducing agent of vanadium, in the presence of a phosphorus source, is an organic medium which comprises (a) isobutyl alcohol or a mixture of isobutyl alcohol and benzyl alcohol, and (b) a polyol in the weight ratio (a) to (b) of 99:1 to 5:95. Most preferred polyols are the $C_{2-4}$-alkanediols 1,2-ethanediol, 1,2-propanediol, 1,3-propanediol and 1,4-butanediol. The preferred mixture of alcohols contains 5 to 30 mol % of polyol with respect to isobutyl alcohol.

WO 00/72963 discloses that the catalyst precursor, even after drying, contains some percent of organic compounds from the organic reaction medium, which is not easily removed. This percentage of organic compounds which remains trapped in the precursor is a fundamental parameter which can positively affect the performance characteristics of the active catalyst obtained after the thermal treatment. WO 00/72963 teaches a method for controlling the carbon content in a vanadium/phosphorus mixed oxide catalyst precursor in order to provide a superior catalyst precursor which, when activated, leads to superior results in the conversion of non-aromatic hydrocarbons to maleic anhydride.

We have now discovered that it is possible to further improve the performance of the catalyst by adding small amounts of Nb compounds or salts to the mixture for the preparation of the catalyst precursor, which mixture includes a vanadium source, a phosphorus source, an organic medium capable of acting as a solvent and a reducing agent, and an additive selected from the group consisting of benzyl alcohol and polyols, provided that the thermal treatment of the precursor is carried out in the presence of steam, following a procedure similar to that described in EP 0 804 963 A1 (assigned to Lonza).

EP 0 804 963 A1 teaches to perform the calcination and activation following the steps of:

a) Initial heating of the catalyst precursor from room temperature to a temperature not to exceed about 250° C., b) further heating under superatmospheric pressure from about 200° C. to a temperature of from at least 380° C. to 600° C., c) maintaining the temperature reached at stage b) under superatmospheric pressure and d) cooling the activated catalyst.

When, after a precalcination step at 200 to 330° C., this calcination and activation procedure, and in particular steps b) to d), is followed, the final catalyst is characterized by enhanced activity with respect to the same catalyst when prepared in the absence of Nb. When thermal treatments other than that described in EP 0 804 963 A1 are employed, the positive effect of Nb on catalytic performance is not observed, or, on the contrary, a negative effect is observed.

According to the present invention it is possible to exploit at best the positive effect of Nb on the catalytic performance of the vanadyl pyrophosphate when the calcination and activation treatment of the precursor is carried out under specific conditions outside the reactor, so that the activated catalyst, when loaded into the reactor, exhibits optimal catalytic performance from the very beginning. This represents a significant advantage with respect to the prior art due to the absence of a period of calcination and activation of the catalyst inside the reactor (with loss of production) and to catalytic performances (conversion of n-butane and the yield of maleic anhydride) at optimal values since the beginning.

As a source of vanadium, a tetravalent or pentavalent vanadium compound may be applied. Representative examples, although not limiting, are vanadium tetrachloride ($VCl_4$), vanadium oxytribromide ($VOBr_3$), vanadium pentoxide ($V_2O_5$), vanadyl phosphate ($VOPO_4 \cdot n\ H_2O$) and vanadium tetraoxide ($V_2O_4$). Vanadium pentoxide is the preferred vanadium source.

Niobium sources can be all the salts and compounds available, such as $NbCl_5$, Nb oxohydrate, or Nb ammonium oxalate complex.

In addition to Nb, which is the promoter of choice of the present application, the precursor may be accompanied by promoter elements selected from the groups IA, IB, IIA, IIB, IIIA, IIIB, IVA, IVB, VA, VB, VIA, VIB and VIIIA of the periodic table of elements, or mixtures thereof. Preferred additional promoter elements are selected from the group consisting of zirconium, bismuth, lithium, molybdenum, boron, zinc, titanium, iron and nickel.

Orthophosphoric acid ($H_3PO_4$) is the preferred phosphorus source.

The preferred organic medium, acting both as a solvent and a reducing agent, as described in patent application WO 00/72963, comprises (a) isobutyl alcohol or a mixture of isobutyl alcohol and benzyl alcohol, and (b) a polyol in the weight ratio (a) to (b) of 99:1 to 5:95. Most preferred polyols are the $C_{2-4}$-alkanediols 1,2-ethanediol, 1,2-propanediol, 1,3-propanediol and 1,4-butanediol. The preferred mixture of alcohols contains 5 to 30 mol % of polyol with respect to isobutyl alcohol.

In a preferred embodiment, the vanadium source, together with the phosphorus source, is suspended in the organic medium and the mixture is kept under agitation at a temperature of 90 to 200° C., more preferably 100 to 150° C. over a period of 1 h to 24 h.

The ratio of niobium source to vanadium source is such that the V/Nb atomic ratio is in the range between 250:1 and 60:1.

The ratio of vanadium source to phosphorus source in the preparation mixture is preferably such that the P/V atomic ratio is in the range of 1:1 to 1.8:1, more preferably 1.1:1 to 1.6:1. When employing V/Nb atomic ratios lower than 100, better results are obtained operating with a ratio of vanadium source to phosphorus source such that the P/V atomic ratio in the preparation mixture in the range 1.3:1 to 1.6:1.

After precipitation, the precursor vanadyl acid orthophosphate is filtered, washed and subsequently dried, preferably at a temperature of 120 to 200° C., and precalcined at a temperature of 200 to 330° C.

In a preferred embodiment, the precursor vanadyl acid orthophosphate can be described by the formula (VO)$HPO_4 \cdot \alpha\ H_2O \cdot M_m P_p O_y$, wherein M is Nb and optionally one promoter element selected from the groups IA, IB, IIA, IIB, IIIA, IIIB, IVA, IVB, VA, VB, VIA, VIB and VIIIA of the periodic table of elements, or of mixtures of such elements, a is a number of from 0.3 to 0.7, m is a number of from 0.004 to 0.017, p is a number of from 0.004 to 0.017 and y corresponds to the amount of oxygen necessary to satisfy the valence requirements of all elements present.

The precalcined precursor, prior to the activation treatment, may be formed into convenient shapes for the final application. Such procedures may include wet grinding to a specific particle size, the addition of additives to improve attrition resistance, and the formation of a convenient shape. Microspheres, which are most suitable for the application of the catalyst in a fluidized bed, can be obtained by spray drying as described for instance in U.S. Pat. No. 4,654,425. For fixed bed reactors the catalyst can be formed in the desired shape by tabletting or extrusion.

The further transformation of the precalcined precursor into the active catalyst is performed by a heat treatment similar to that described in EP 0 804 963 A1, by (a) heating under super-atmospheric pressure and in a steam-containing atmosphere to a temperature of 380 to 600° C., (b) maintaining the temperature reached in step (a) under superatmospheric pressure and (c) cooling the thus activated catalyst. This heat treatment is preferably carried out outside the reactor used for the production of maleic anhydride, in a fluidized bed or in an oven.

The product obtained after activation has the structure of the active catalyst vanadyl pyrophosphate and is ready to be loaded into the reactor and applied for the conversion of non-aromatic hydrocarbons such as butane to maleic anhydride.

Such processes are well known in the art, e.g. U.S. Pat. Nos. 4,594,433, 5,137,860 or 4,668,652.

The non-aromatic hydrocarbon, selected from aliphatic $C_{4-10}$ hydrocarbons, preferably n-butane, is fed with oxygen or an oxygen containing gas to the reactor, at a temperature from about 320 to 500° C., and converted to maleic anhydride.

The conversion can take place in a fixed bed or a fluidized bed reactor, preferably a fluidized bed reactor is used. The following examples are given by way of illustration only and are not construed as to in any way limit the invention.

In the following examples, the carbon content in the precursor was determined by combustion in pure oxygen at high temperature using the apparatus and procedure described below and detection of the carbon dioxide formed by infrared analysis.

Apparatus: ELTRA 900CS

Measuring range: 0.001-100 wt % C

Sensitivity: 0.0001 wt % C

Time per sample: 90 s

Sample size: 0.1-0.5 g

Oven temperature: 400-1500° C.

Oxygen purity: 99.5% min.

Oxygen flow rate: 4 L/min

Procedure:

The furnace was heated up to 1330° C. and oxygen flow was opened 10 minutes before starting the analysis. High carbon content detector was selected and calibrated with standard samples having known carbon content. The sample size used was 150±10 mg.

EXAMPLE 1

V/Nb Atomic Ratio 160

Into a 30 L reactor fitted with thermometer, mechanical stirrer and distillation column with reflux condenser and water separator, were introduced 1,968 g of $V_2O_5$, 65 g of niobium ammonium oxalate and 2,484 g of 100% $H_3PO_4$ (P/V atomic ratio=1.17) suspended in 16,700 g of a mixture of isobutyl alcohol and 1,4-butanediol (80:20). The mixture was kept under agitation and heated up to reflux and left at these conditions for 8 hours. The colour of the mixture changed from red-brown to light green.

The mixture was cooled to room temperature, then filtered and washed with isobutyl alcohol. Then the solid was dried at 150° C. and precalcined at 300° C. The carbon content in the precalcined precursor was 1.7 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

EXAMPLE 2

V/Nb Atomic Ratio 200

The procedure of Example 1 was followed with the exception that 52 g of niobium ammonium oxalate were used. The carbon content of the precalcined precursor was 1.8 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP0 804 963 A1.

EXAMPLE 3

V/Nb Atomic Ratio 120

The procedure of Example 1 was followed with the exception that 87 g of niobium ammonium oxalate were used. The carbon content of the precalcined precursor was 1.7 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

COMPARATIVE EXAMPLE 1

No Nb

The procedure of Example 1 was followed with the exception that no niobium ammonium oxalate was used. The carbon content of the precalcined precursor was 1.8 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

COMPARATIVE EXAMPLE 2

No Nb, No 1,4-butanediol

The procedure of Example 1 was followed with the exception that no niobium ammonium oxalate was used and no 1,4-butanediol was loaded into the reactor. The carbon content of the precalcined precursor was 0.5 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

COMPARATIVE EXAMPLE 3

V/Nb Atomic Ratio 25

The procedure of Example 1 was followed with the exception that 416 g of niobium ammonium oxalate were used. The carbon content of the precalcined precursor was 2.0 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP0804963 A1.

EXAMPLE 4

V/Nb Atomic Ratio 80, P/V=1.17

The procedure of Example 1 was followed with the exception that 130 g of niobium ammonium oxalate were used. The carbon content of the precalcined precursor was 1.8 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

EXAMPLE 5

V/Nb Atomic Ratio 80, P/V=1.46

The procedure of Example 4 was followed with the exception that 3,092 g of $H_3PO_4$ (100%) were used. The carbon content of the precalcined precursor was 2.0 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

COMPARATIVE EXAMPLE 4

No 1,4-butanediol

The procedure of Example 1 was followed with the exception that no 1,4-butanediol was loaded into the reactor. The carbon content of the precalcined precursor was 0.5 wt %.

The solid was then shaped with milling and spray-drying steps to get the typical fluidized bed sphere shape as described in Example 1 of U.S. Pat. No. 4,654,425.

The solid was calcined in a hydrothermal fluidized bed as described in Example 4 of EP 0 804 963 A1.

COMPARATIVE EXAMPLE 5

No Hydrothermal Treatment

The procedure of Example 1 was followed. The carbon content of the precalcined precursor was 1.8 wt %.

The solid was then shaped with milling and spray-drying steps to get the typical fluidized bed sphere shape as described in Example 1 of U.S. Pat. No. 4,654,425.

The solid was calcined according to the following procedure:
nitrogen atmosphere
3 K/min
final t=550° C., kept for 6 hours Fluidized Bed Catalytic Tests The catalysts prepared in Examples 1-5 and in Comparative Examples 1-5 were tested in a pilot metal fluidized bed reactor under the following conditions:
catalyst loaded into the reactor 1000 cm³
air flow rate 556 NL/h
n-butane feed
  4.3 vol %
  65 g/h
pressure 3.0 bar (2.0 barg)

The performances of the catalysts are summarized in Table 1.

TABLE 1

| Example No. | t[° C.] | Conversion [%] | MA Yield [wt %] | MA molar Selectivity [%] |
|---|---|---|---|---|
| 1 | 404 | 81 | 92 | 67 |
| 2 | 420 | 82 | 89 | 64 |
| 3 | 397 | 81 | 91 | 66 |
| Comp. 1 | 422 | 81 | 85 | 62 |
| Comp. 2 | 424 | 80 | 79 | 59 |
| Comp. 3 | 370 | 85 | 49 | 34 |
| 4 | 374 | 81 | 76 | 56 |
| 5 | 395 | 80 | 89 | 66 |
| Comp. 4 | 412 | 80 | 86 | 64 |
| Comp. 5 | 401 | 29 | 28 | 57 |

Examples 4 and 5 show that in the presence of Nb with a V/Nb atomic ratio lower than 100, when the P/V atomic ratio in the preparation mixture is lower than the optimal one, the performance of the catalyst is worse. In this case the performance of the catalyst can be improved by feeding to the reactor, together with air and butane, small amounts of phosphorus compounds such as organic phosphites or organic phosphates (this is a well known commercial practice usually applied to keep constant in time the performance of the catalyst). During the test of the catalyst of Example 4, after few days of non satisfactory performance, triethyl phosphite was added to the reaction mixture fed to catalyst. After few days a yield of 86 wt % was obtained at a temperature of 395° C. and at a conversion of butane of 80%.

EXAMPLE 6

V/Nb Atomic Ratio 160, Fixed Bed

The preparation of example 1 was followed for the preparation of the precalcined precursor. The carbon content of the precalcined precursor was 1.7 wt %.

The precalcined powder precursor was mixed with 4% of graphite and formed into 4.8×4.8 mm ring tablets with a 1.7 mm hole in the centre. The pellets of the precalcined precursor were activated in hydrothermal conditions heating from room temperature to 430° C. in controlled atmosphere: oxygen content was 13% at the beginning and 5% in the final step, steam content was about 50%.

COMPARATIVE EXAMPLE 6

V/Nb Atomic Ratio 45, Fixed Bed

The procedure of Example 6 was followed with the exception that 51.5 g of niobium ammonium oxalate were used.

The carbon content of the precalcined precursor was 1.8 wt %.

The precalcined powder precursor was formed and activated as described in Example 6.

COMPARATIVE EXAMPLE 7

No Nb, No 1,4-butanediol, Fixed Bed

The procedure of Comparative Example 2 was followed.

The carbon content of the precalcined precursor was 0.5 wt %.

The precalcined powder precursor was formed and activated as described in Example 6.

Fixed Bed Catalytic Tests

The catalysts prepared in Example 6 and in Comparative Examples 7 and 8 were tested in a pilot fixed bed tubular reactor (h=380 cm, ID=2.1 cm) under the following conditions:
    catalyst loaded into the reactor 750 g
    air flow rate 2650 NL/h
    n-butane feed
        1.7 vol %
        118 g/h the performances of the catalysts are summarized in Table 2.

TABLE 2

| Example No. | t[° C.] | Conversion [%] | MA Yield [wt %] | MA molar Selectivity [%] |
|---|---|---|---|---|
| 6 | 405 | 80 | 95 | 70 |
| Comp. 6 | 400 | 81 | 88 | 64 |
| Comp. 7 | 424 | 76 | 87 | 68 |

The invention claimed is:

1. A process for the preparation of a modified vanadium/phosphorus mixed oxide catalyst comprising vanadyl pyrophosphate as main component and niobium as a promoter element in an amount corresponding to an atomic ratio of vanadium to niobium in the range of 250:1 to 60:1, said process comprising the steps of (i) providing a reaction mixture comprising a vanadium source, a niobium source, a phosphorus source, an organic medium capable of acting as a solvent and a reducing agent, and an additive selected from the group consisting of benzyl alcohol and polyols, (ii) heating said reaction mixture to form a modified vanadyl acid orthophosphate catalyst precursor, (iii) isolating and drying said vanadyl acid orthophosphate catalyst precursor, (iv) pre-calcining said dried vanadyl acid orthophosphate catalyst precursor at a temperature of 200 to 330° C., (v) optionally shaping said vanadyl acid orthophosphate catalyst precursor into a shape suitable for the bed and reactor type wherein the finished catalyst is to be used, and (vi) calcining and activating said vanadyl acid orthophosphate catalyst precursor by (a) heating under superatmospheric pressure and in a steam-containing atmosphere to a temperature of 380 to 600° C., (b) maintaining the temperature reached in step (a) under superatmospheric pressure and (c) cooling the activated catalyst.

2. The process of claim 1, wherein the vanadium source is vanadium pentoxide.

3. The process of claim 2, wherein the phosphorus source is phosphoric acid.

4. The process of claim 3, wherein the organic medium comprises isobutyl alcohol and a polyol in the weight ratio of 99:1 to 5:95, preferably 5 to 30 mol % of polyol with respect to isobutyl alcohol.

5. The process of claim 4, wherein the polyol is a $C_{2-4}$ alkanediol, preferably 1,2-ethanediol, 1,2-propanediol, 1,3-propanediol or 1,4-butanediol.

6. The process of claim 5, wherein the P/V atomic ratio is 1:1 to 1.8:1, preferably 1.1:1 to 1.6:1.

7. The process of claim 6, wherein, in step (ii), the mixture is kept under agitation at a temperature of 90 to 200° C., preferably 100 to 150° C. over a period of 1 h to 24 h.

8. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 7, wherein the niobium improves selectivity to maleic anhydride.

9. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 6, wherein the niobium improves selectivity to maleic anhydride.

10. The process of claim 5, wherein, in step (ii), the mixture is kept under agitation at a temperature of 90 to 200° C., preferably 100 to 150° C. over a period of 1 h to 24 h.

11. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 5, wherein the niobium improves selectivity to maleic anhydride.

12. The process of claim 4, wherein the P/V atomic ratio is 1:1 to 1.8:1, preferably 1.1:1 to 1.6:1.

13. The process of claim 4, wherein, in step (ii), the mixture is kept under agitation at a temperature of 90 to 200° C., preferably 100 to 150° C. over a period of 1 h to 24 h.

14. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 4, wherein the niobium improves selectivity to maleic anhydride.

15. The process of claim 3, wherein the polyol is a $C_{2-4}$ alkanediol, preferably 1,2-ethanediol, 1,2-propanediol, 1,3-propanediol or 1,4-butanediol.

16. The process of claim 3, wherein the P/V atomic ratio is 1:1 to 1.8:1, preferably 1.1:1 to 1.6:1.

17. The process of claim 3, wherein, in step (ii), the mixture is kept under agitation at a temperature of 90 to 200° C., preferably 100 to 150° C. over a period of 1 h to 24 h.

18. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 3, wherein the niobium improves selectivity to maleic anhydride.

19. The process of claim 2, wherein the organic medium comprises isobutyl alcohol and a polyol in the weight ratio of 99:1 to 5:95, preferably 5 to 30 mol % of polyol with respect to isobutyl alcohol.

20. The process of claim 2, wherein the polyol is a $C_{2-4}$ alkanediol, preferably 1,2-ethanediol, 1,2-propanediol, 1,3-propanediol or 1,4-butanediol.

21. The process of claim 2, wherein the P/V atomic ratio is 1:1 to 1.8:1, preferably 1.1:1 to 1.6:1.

22. The process of claim 2, wherein, in step (ii), the mixture is kept under agitation at a temperature of 90 to 200° C., preferably 100 to 150° C. over a period of 1 h to 24 h.

23. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 2, wherein the niobium improves selectivity to maleic anhydride.

24. The process of claim 1, wherein the phosphorus source is phosphoric acid.

25. The process of claim 1, wherein the organic medium comprises isobutyl alcohol and a polyol in the weight ratio of 99:1 to 5:95, preferably 5 to 30 mol % of polyol with respect to isobutyl alcohol.

26. The process of claim 1, wherein the polyol is a $C_{2-4}$ alkanediol, preferably 1,2-ethanediol, 1,2-propanediol, 1,3-propanediol or 1,4-butanediol.

27. The process of claim 1, wherein the P/V atomic ratio is 1:1 to 1.8:1, preferably 1.1:1 to 1.6:1.

28. The process of claim 1, wherein, in step (ii), the mixture is kept under agitation at a temperature of 90 to 200° C., preferably 100 to 150° C. over a period of 1 h to 24h.

29. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 1, wherein the niobium improves selectivity to maleic anhydride.

30. A process for the production of maleic anhydride by partially oxidizing n-butane in an oxygen containing gas mixture in the presence of a heterogeneous catalyst, wherein the catalyst is a niobium containing vanadium/phosphorus mixed oxide catalyst according to claim 29.

31. The process of claim 1, wherein the vanadium source is a pentavalent vanadium compound.

32. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 31, wherein the niobium improves selectivity to maleic anhydride.

33. A process for the production of maleic anhydride by partially oxidizing n-butane in an oxygen containing gas mixture in the presence of a heterogeneous catalyst, wherein the catalyst is a niobium containing vanadium/phosphorus mixed oxide catalyst according to claim 32.

34. The process of claim 1, wherein the organic medium comprises:
   (a) isobutyl alcohol or a mixture of isobutyl alcohol and benzyl alcohol; and
   (b) a polyol
in the weight ratio (a) to (b) of 99:1 to 5:95.

35. A modified vanadium/phosphorus mixed oxide catalyst for the partial oxidation of n-butane to maleic anhydride, comprising vanadyl pyrophosphate as main component and niobium as a promoter element in an amount corresponding to an atomic ratio of vanadium to niobium in the range of 250:1 to 60:1, obtainable by the process of claim 34, wherein the niobium improves selectivity to maleic anhydride.

36. A process for the production of maleic anhydride by partially oxidizing n-butane in an oxygen containing gas mixture in the presence of a heterogeneous catalyst, wherein the catalyst is a niobium containing vanadium/phosphorus mixed oxide catalyst according to claim 35.

* * * * *